(12) United States Patent
Priori et al.

(10) Patent No.: US 10,945,642 B2
(45) Date of Patent: Mar. 16, 2021

(54) APPARATUS AND METHOD FOR MONITORING DISEASE PROGRESSION IN A SUBJECT

(71) Applicant: KONINKLIJKE PHILIPS N.V., Eindhoven (NL)

(72) Inventors: Rita Priori, Cambridge (GB); Mareike Klee, Straelen (DE); Rene Martinus Maria Derkx, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 354 days.

(21) Appl. No.: 16/069,623

(22) PCT Filed: Jan. 12, 2017

(86) PCT No.: PCT/EP2017/050599
§ 371 (c)(1),
(2) Date: Jul. 12, 2018

(87) PCT Pub. No.: WO2017/121819
PCT Pub. Date: Jul. 20, 2017

(65) Prior Publication Data
US 2019/0008415 A1    Jan. 10, 2019

(30) Foreign Application Priority Data
Jan. 14, 2016    (EP) .................................... 16151337

(51) Int. Cl.
*A61B 5/113* (2006.01)
*A61B 5/11* (2006.01)
(Continued)

(52) U.S. Cl.
CPC ............ *A61B 5/113* (2013.01); *A61B 5/0816* (2013.01); *A61B 5/1118* (2013.01);
(Continued)

(58) Field of Classification Search
None
See application file for complete search history.

(56) References Cited

U.S. PATENT DOCUMENTS

| | | |
|---|---|---|
| 2012/0330114 A1 | 12/2012 | Cheung |
| 2013/0030258 A1 | 1/2013 | Cheung et al. |
| 2015/0324541 A1 | 11/2015 | Cheung et al. |

FOREIGN PATENT DOCUMENTS

| | | |
|---|---|---|
| WO | WO2012020433 A1 | 2/2012 |
| WO | WO2013036677 A1 | 3/2013 |

(Continued)

OTHER PUBLICATIONS

Zwerink, M. et al., "Relationship Between Daily Physical Activity and Exercise Capacity in Patients with COPD", Respiratory Medicine, 2013, 107, pp. 242-248.

*Primary Examiner* — Marjan Fardanesh
(74) *Attorney, Agent, or Firm* — Daniel H. Brean (57) ABSTRACT

An apparatus comprises an activity monitor for measuring physical activity of a subject. The activity monitor is configured to obtain a first set of physical activity data over a first time period, for example during the day, and a second set of physical activity data over a second time period, for example during the night. A processor processes the data obtained by the activity monitor to calculate a physical activity ratio which is the ratio of the physical activity measured during the first time period to the physical activity measured in the second time period. The processor also calculates a first overall value which represents an activity level of the subject during the first time period. The physical activity ratio together with the first overall value may be used to assess the severity of symptoms of COPD displayed by a subject or to identify respiratory disease comorbidity information for example psychological issues such as low motivation, or sleep quality issues displayed by the subject.

15 Claims, 5 Drawing Sheets

(51) Int. Cl.
  *G16H 50/20* (2018.01)
  *G16H 80/00* (2018.01)
  *A61B 5/08* (2006.01)
  *A61B 5/00* (2006.01)

(52) U.S. Cl.
  CPC ........... *A61B 5/4842* (2013.01); *G16H 50/20* (2018.01); *G16H 80/00* (2018.01); *A61B 5/08* (2013.01); *A61B 5/7271* (2013.01); *A61B 5/746* (2013.01)

(56) References Cited

FOREIGN PATENT DOCUMENTS

WO WO2015197808 A1 12/2015
WO WO-2015197809 A1 * 12/2015 ........... A61B 5/0022

\* cited by examiner

APPARATUS AND METHOD FOR MONITORING DISEASE PROGRESSION IN A SUBJECT

CROSS-REFERENCE TO RELATED APPLICATIONS

This patent application claims the priority benefit under 35 U.S.C. § 371 of international patent application no. PCT/EP2017/050599, filed Jan. 12, 2017, which claims the benefit of European Patent Application No. 16151337.9, filed on Jan. 14, 2016, the contents of which are herein incorporated by reference.

FIELD OF THE INVENTION

The present invention relates to an apparatus and method for monitoring disease progression in a subject, and in particular to an apparatus for monitoring the activity of a subject to determine the health status of a subject.

BACKGROUND OF THE INVENTION

Chronic obstructive pulmonary disease (COPD) refers to chronic lung diseases that cause limitations in lung air flow. COPD is progressive and irreversible; it is characterized by airflow obstruction caused by a combination of airway and parenchymal damage resulting from chronic inflammation of the airways, lung tissue and pulmonary blood vessels. The inflammation seen in COPD patients differs from that seen in asthma; the primary cause of COPD is tobacco smoke.

COPD symptoms often lead to disability and impaired quality of life. Pharmacological and other therapies for treating COPD patients may have limited or no impact on airflow obstruction. Exacerbations, the rapid and sustained worsening of symptoms beyond normal day-to-day variations, often occur in patients with COPD. In addition, comorbidities, such as cardiovascular or psychology-related comorbidities, have an important impact on disease severity and survival, as well as the health status of a patient.

Although COPD has been predicted to become the third leading cause of death and disease worldwide by 2020, it is still highly underdiagnosed and diagnosis occurs only at a stage when symptoms become very severe. There is no single diagnostic test for COPD. Making a diagnosis relies on a number of elements, including clinical judgement based on a combination of history and physical examination to determine symptoms and signs typical of COPD. Diagnosis is supported by spirometry, which is used to confirm the presence of airflow obstruction.

Spirometry involves measuring the volume and flow of air that can be inhaled and exhaled by a patient. Forced expiratory volume in one second (FEV1) and forced vital capacity (FVC) are parameters measured in spirometry. FEV1 is the volume of air that has been exhaled at the end of the first second of force expiration. FVC is the volume of air exhaled after deepest inhalation from a maximally forced expiratory effort. Currently, to confirm that a patient's symptoms are indicative of COPD using spirometry, the ratio of FEV1 to FVC after bronchodilator medication has been administered must be lower than 0.7.

Recent studies have shown that patients with clinically stable COPD are relatively physically inactive compared to age-matched control subjects. Potential reasons for this lower physical activity of COPD patients are breathlessness and fatigue associated with muscular force exhaustion following exercise. Further, the level of physical activity decreases even further following a hospitalization for an exacerbation of COPD. However, physical activity is an important tool for managing COPD. An active lifestyle and regular physical activity has shown to be positively associated with outcomes such as exercise capacity and health-related quality of life.

It is likely that the reason for this lack of physical activity in patients with COPD is associated with a downward spiral of symptom-induced inactivity leading to deconditioning and muscle weakness. Physical fitness, which can be measured by various exercise tests, comprises a set of attributes that relate to the ability to perform physical activity. The six minute walk test is a well-known way to assess exercise capacity. However, it has been shown that although a moderate correlation exists between the six minute walk distance associated with a patient and objectively measured physical activity, the six minute walk test could be of limited value to reliably identify physically inactive COPD patients. In other words, exercise capacity is not a reliable indicator of general physical activity levels, since a patient may be capable of performing physical activity but exhibit low physical activity.

Although an early diagnosis of COPD and prompt initiation of therapy may reduce and control disease progression, the use of spirometry as the only tool for diagnosis and monitoring of disease progression has several limitations. First of all, the procedure relies on the patient's performance and is therefore to some extent dependent on the will of the patient. Moreover, spirometry is a singular event and consequently does not allow for a continuous and unobtrusive measure of disease progression and the general health status of a patient. Therefore, spirometry cannot provide information about whether an exacerbation has occurred. Further still, spirometry only addresses the respiratory status of the patient and does provide information that indicates whether other comorbidities are present e.g. psychology-related comorbidities.

In case a positive diagnosis of COPD is made, apart from pharmacological therapy, non-pharmacological interventions such as pulmonary rehabilitation or physical activity maintenance programmes may be appropriate. The success and maintenance of the benefits resulting from such interventions is highly dependent on, first of all, the health status of the patient (since physical capacity may decrease if an exacerbation occurs) but also the short term and long term motivation of the patient, together with other psycho-social factors. Currently, a tool that can help objectively assess whether a decrease in physical activity is due to exercise limitation, lack of motivation or deterioration is not available.

There is therefore a need for an improved way to assess the health status of a patient with COPD.

SUMMARY OF THE INVENTION

The invention is defined by the claims.

According to examples in accordance with an aspect of the invention, there is provided an apparatus, comprising:
   an activity monitor for measuring the physical activity of a subject; and
   a processor for processing data obtained by the activity monitor, wherein the processor is configured to:
      calculate a first overall value based on a first set of physical activity data associated with a first time period;

calculate a physical activity ratio based on the first set of physical activity data and a second set of physical activity data associated with a second time period; and determine respiratory disease severity information and/or respiratory disease comorbidity information based on a combination of the physical activity ratio and the first overall value.

The apparatus is adapted to measure a physical activity ratio. This has been found to be a parameter suitable for indicating the severity of COPD symptoms suffered by the subject. The activity monitor obtains information about the physical activity of the subject over time, including a first data set and a second data set. The first data set may, for example, correspond to the level of physical activity of the subject during the daytime, while the subject is awake. The second data set may, for example, correspond to the level of physical activity of the subject during the night-time, while the subject is asleep. The terms daytime and night-time may refer to any subset of consecutive hours during a twenty four hour period, wherein the hours in the daytime subset are different to the night-time subset. The activity monitor transmits physical activity data to the processor, which processes the physical activity data to calculate the physical activity ratio. By analysing the physical activity ratio, symptom severity can be assessed. The physical activity ratio is determined by calculating the ratio of the physical activity of the subject during the first time period (e.g. day) to the physical activity of the subject during the second time period (e.g. night). This ratio provides an accurate indicator of the severity of the medical condition suffered by the subject, and can also be used to support an assessment about whether a decrease in physical activity is due to exercise limitation caused by severe COPD symptoms or other issues such as lack of motivation or sleep problems. Further, the apparatus allows symptom severity to be measured continuously. The processor also calculates a first overall value which represents the subject's physical activity during the first time period. The first overall value may be a measure of the total movement over the time period or may be a measure based on the average movement over the first time period. By taking both the physical activity ratio and the first overall value into account, the apparatus can be used to support an assessment of severity of a disease and/or other issues, for example psychological issues (such as low motivation) or sleep quality issues.

The processor is further configured to determine respiratory disease severity information and/or respiratory disease comorbidity information based on a combination of the physical activity ratio and the first overall value.

In this way, the processor may determine the health status of a subject based on a combination of information about the level of physical activity performed by the subject during the day and the ratio of the level of physical activity performed by the subject during the day to the level of physical activity performed by the subject during the night.

In particular, the processor may be configured to determine respiratory disease severity information and/or respiratory disease comorbidity information based on a comparison of the physical activity ratio and the first overall value.

The processor may determine respiratory disease severity information and/or respiratory disease comorbidity information based on the magnitude of the first overall value and the magnitude of the physical activity ratio.

The processor may be configured to output the respiratory disease severity information and/or respiratory disease comorbidity information.

The processor may determine the health status of the patient based on a combination of the first overall value and the physical activity ratio and may output this information. The combination of the physical activity ratio and the first overall value may indicate the level of disease severity and whether respiratory disease comorbidities (e.g. low motivation or sleep issues) are present.

In general, the first overall value alone does not necessarily provide an accurate indicator of physical activity capacity, and by implication therefore of a level of disease severity. A relatively lower first overall value for example (indicating lower physical activity during the first time period) may be the result for instance of low motivation or other psychological factors.

By taking into account a combination of both the first overall value and the physical activity ratio in determining disease severity and/or comorbidity information, a more accurate picture of the patient's health is determined. In particular, an assessment can be made as to whether a relatively lower (or higher) first overall value is due to physical exercise capacity (and therefore indicative of higher disease severity) or due instead to motivational issues for instance. Accurate determination of disease severity and/or comorbidity information may only be determined through combined consideration of both of the first overall value and the physical activity ratio.

In particular, the first overall value may in examples be compared with or against the physical activity ratio, to thereby make a determination of disease severity and/or comorbidity information. Where the first overall value for instance indicates a relatively low activity level, this may be compared with the activity ratio to thereby make an assessment as to whether this is due to low physical activity capacity, or rather due to low motivation or other psychological or social factors.

The respiratory disease severity information may relate to chronic obstructive pulmonary disease.

The processor may be configured to:

calculate a second overall value based on the second set of physical activity data; and calculate the physical activity ratio by dividing the first overall value by the second overall value.

In this case, the physical activity ratio is the ratio of the first overall value and the second overall value. The processor may obtain physical activity data that represents the physical activity of the subject over the first time period and the second time period. The physical activity data may comprise data that represents the activity level of the subject during sub-periods of the time period. For example, the first time period may be a period of twelve hours and the physical activity data may comprise information about the level of activity performed on a minute-by-minute, hourly or bi-hourly basis. The activity level may be determined by measuring a movement related measure. The processor may process each data set obtained by the physical activity monitor to calculate a value which represents the overall level of activity for the corresponding data set. The first and second overall value may represent the average level of physical activity over the first and second time periods respectively. Alternatively, the processor may determine a measure based on a total of the measured movement for each data set. The processor may calculate any value which is representative of the overall level of physical activity performed by the subject over the time period over which the data set was obtained.

The activity monitor may comprise an accelerometer. In use, the accelerometer may be arranged such that the output of the accelerometer is representative of the physical activity performed by the subject.

The apparatus may further comprise a controller configured to control the activity monitor to obtain a first set of data during the day and a second set of data during the night. For example, the activity monitor may obtain a first set of data over a time period when the subject is usually awake, and may obtain a second set of data over a time period when the subject is usually asleep, based on timing information supplied by a user (e.g. the subject, or a care provider).

The processor may be configured to determine, for each of the first and second data set, whether the data set corresponds to daytime physical activity or night-time physical activity. The activity monitor may obtain physical activity data and the processor may categorise the data based on time information included in the data itself.

Alternatively, the physical activity monitor may measure physical activity against time. Therefore, the physical activity data obtained by the physical activity monitor may include timing information, as well as information about the physical activity level. The processor may be configured to process the physical activity data to determine the time at which data was obtained and to divide the data into sets, wherein each set corresponds to a different time period. The processor may be pre-programmed with a definition of daytime hours (e.g. 07.00 am to 23.00 pm) and night-time hours (e.g. 23.01 pm to 06.59 am). The processor may then be configured to select a first data set from the physical activity data, wherein the first data set comprises data that was obtained during a first time period corresponding to daytime hours, and to select a second data set from the data obtained by the physical activity monitor, wherein the second data set corresponds to night-time hours. Alternatively, the processor may process data based on a sensor input. For example, the processor may process a light level signal to determine whether the data is obtained during the daytime or the night-time.

The apparatus may further comprise a controller configured to control the physical activity monitor to obtain a first set of physical activity data while the subject is awake, and to obtain a second set of physical activity data while the subject is asleep.

The apparatus may be adapted to allow a user to manually control the apparatus to switch between a daytime measurement mode (when the subject is awake) and night-time measurement mode (when the subject is asleep). Alternatively, the apparatus may be configured to perform day and night-time measurements automatically based on pre-programmed information about the subject's normal sleeping patterns. Alternatively, the apparatus may be configured to determine whether data is obtained during the daytime or the night-time based on a sensor input, such as a light signal obtained by a light sensor.

The processor may be configured to determine respiratory disease severity information based on the physical activity ratio and an activity ratio threshold value.

The activity ratio threshold value may represent a baseline activity ratio level. The activity ratio threshold may correspond to an average activity ratio level of a patient group. For instance, if the ratio is equal to or larger than the average level of a group of patients with respiratory disease symptoms of low severity, the severity of symptoms of the subject may be low. The processor may be pre-programmed with an activity ratio threshold value. If the measured physical activity ratio is lower than the threshold value, this may indicate that the subject has severe symptoms and reduced exercise capacity. Alternatively, the activity ratio threshold value may be input by the user. The activity ratio threshold may be calculated using a theoretical model and inputting information specific to the subject.

As well as determining respiratory disease severity based on the physical activity ratio and an activity ratio threshold value, the processor may be configured to determine respiratory disease severity information based on the magnitude of the first overall value and the daytime activity threshold value. Therefore, the processor may be configured to determine respiratory disease severity information based on the magnitude of the first overall physical activity value, the daytime physical activity threshold value, the physical activity ratio and the activity ratio threshold value. The daytime activity threshold value may represent a baseline activity level. For example, the daytime activity threshold value may correspond to an average activity level of a patient group. The activity ratio threshold value may represent a baseline activity ratio level. For example, the activity ratio threshold may correspond to an average activity ratio level of a patient group. The processor may be pre-programmed with a daytime activity level threshold value and an activity ratio threshold value. If the measured daytime physical activity (the first overall value) is lower than the daytime activity threshold value and the calculated physical activity ratio is lower than the activity ratio threshold value, this may indicate that the subject has severe symptoms.

The processor may be configured to determine a risk score for indicating respiratory disease symptom severity based on the physical activity ratio. The risk score may reflect the severity of the condition of the subject.

The processor may be configured to determine respiratory disease severity information based the physical activity ratio, the first overall value and a daytime activity threshold value. By taking both the physical activity ratio and the first overall value into account the apparatus can support an assessment of disease severity or other issues for example psychological issues (such as low motivation) or sleep quality issues. The processor may be configured to compare the first overall value to a daytime activity threshold value. The daytime activity threshold value may represent a baseline level of activity expected to be completed by the subject during the first time period. If the first overall value is lower than the daytime activity threshold value, this may indicate that the subject has reduced exercise capacity, caused by disease symptoms. However, the first overall value alone is not an accurate indicator of reduced exercise capacity, since it may be the result of low motivation rather than severe disease symptoms. Information relating to the first overall value may be provided in combination with information about the level of severity indicated by the measured physical activity ratio, to provide a more complete picture of the subject's health status.

The processor may be configured to determine respiratory disease severity information and respiratory disease comorbidity information based on:

the magnitude of the physical activity ratio relative to the magnitude of the activity ratio threshold value; and the magnitude of the first overall value relative to the magnitude of a daytime activity threshold value.

The processor may determine whether the subject has severe disease symptoms causing low activity levels, low motivation, sleep disturbance issues or no disease related issues based on this information.

The processor may be configured to output the determined respiratory disease severity information and/or respiratory disease comorbidity information.

The activity monitor may comprise a strap for attaching the activity monitor to the subject. This may facilitate continuous monitoring of the subject's health status.

According to another aspect of the invention, there is provided a method, comprising:

obtaining a first set of physical activity data by measuring physical activity over a first time period;

obtaining a second set of physical activity data by measuring physical activity over a second time period;

calculating a first overall value based on the first set of physical activity data;

calculating a physical activity ratio based on the first set of physical activity data and the second set of physical activity data, and determine respiratory disease severity information and/or respiratory disease comorbidity information based on a combination of the physical activity ratio and the first overall value The first set of physical activity data may for example include data obtained during the day, and the second set of physical activity data may for example include data obtained during the night. The first set of physical activity data may for example include data obtained while the subject is awake, and the second set of physical activity data may for example include data obtained while the subject is asleep.

The method may further comprise calculating a second overall value for the second set of physical activity data, wherein the physical activity ratio is a ratio of the first overall value and the second overall value.

The overall value may be a value which represents a total measured movement, or it may be a value which represents an average activity level measured over the time period.

According to an aspect of the invention, there is provided a computer program product comprising code means adapted to perform the method described above when said program is run on a computer.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an apparatus comprising an activity monitor for measuring how physically active a subject is. The activity monitor is configured to obtain a first set of physical activity data over a first time period, for example during the day, and a second set of physical activity data over a second time period, for example during the night. A processor processes the data obtained by the activity monitor to calculate a first overall value which represents the activity level of the subject over the first time period and a physical activity ratio. In detail, the processor calculates the ratio of the physical activity measured during the first time period to the physical activity measured in the second time period. For example, the physical activity ratio is the ratio of daytime physical activity to night-time physical activity. The physical activity ratio may be used to assess the severity of COPD symptoms experienced by a subject and to determine the level of disease progression in the subject. Further, the physical activity ratio may be used in combination with the first overall value to determine whether low activity levels are likely to be caused by low physical capability or whether low activity is likely to be associated with low motivation of the subject. The physical activity ratio in combination with the first overall value may also indicate the presence of sleep related issues.

Figure 1:
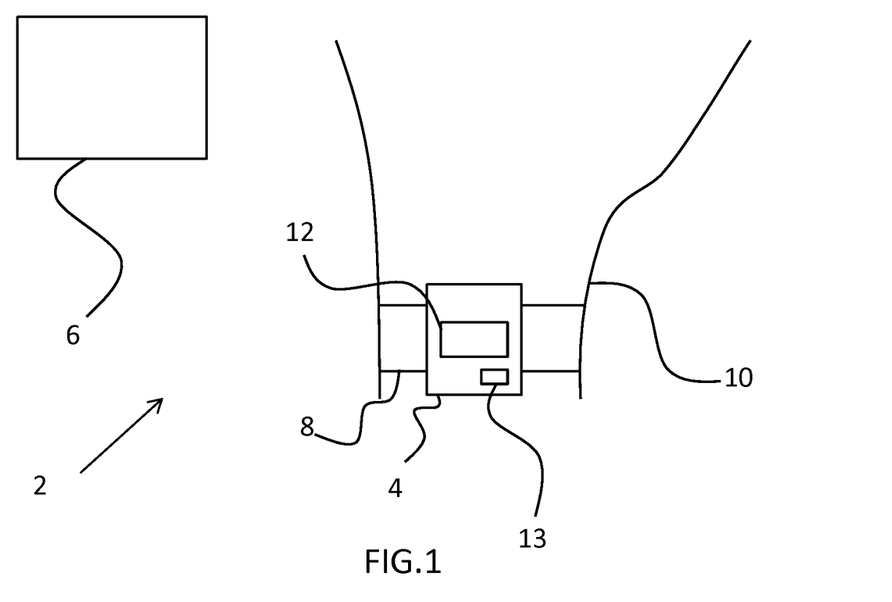
FIG. 1 shows an apparatus according to an example, with an activity monitor attached to a subject's hand.

FIG. 1 shows an apparatus 2 according to the invention. The apparatus 2 is a monitoring system, for monitoring the health of patients with respiratory problems. The apparatus comprises an activity monitor 4 and a remotely located processor 6; the activity monitor 4 and the processor 6 are adapted to communicate with each other for example wirelessly or over a wired connection. The processor may include a display, and an audio output.

The activity monitor 4 is adapted to be worn by a user over a long duration (at least twenty four hours), and comprises a strap 8 for attaching the activity monitor to the subject 10. The activity monitor 4 comprises a motion sensor 12 for measuring the physical activity performed by the subject 10. The motion sensor 12 is, for example, an accelerometer which is adapted to detect movement of the subject's body. In this way, the activity monitor 4 is configured to measure the physical activity of the subject 10, since an output signal of the activity monitor 4 corresponds to physical activity of the subject 10.

The activity monitor comprises a controller 13 which controls the motion sensor 12 to measure physical activity over at least a twenty four hour period, both while the subject 10 is awake and while the subject is asleep.

The processor 6 is configured to associate data obtained by the activity monitor 2 with a first time period or a second time period. For example, the processor 6 may determine that data is daytime data or night-time data according to the time at which the data was obtained.

The processor 6 calculates an overall value for each time period; the overall value represents the activity level performed by the subject during the time period in which the data was obtained. For example, the processor 6 may calculate the total movement measured by the accelerometer for each time period. In preferred examples, the processor 6 calculates the average activity level of the subject over the time period.

The processor may covert the accelerometer output into an activity level using an algorithm. The processor may calculate the activity level by measuring acceleration over discrete time intervals and convert this data to activity "counts". The processing of acceleration data varies among device manufacturers but can be standardized.

The processor 6 calculates a first overall value which represents the overall physical activity of the subject 10 during the daytime and a second overall value which represents the overall physical activity of the subject 10 during the night-time.

Figure 8:
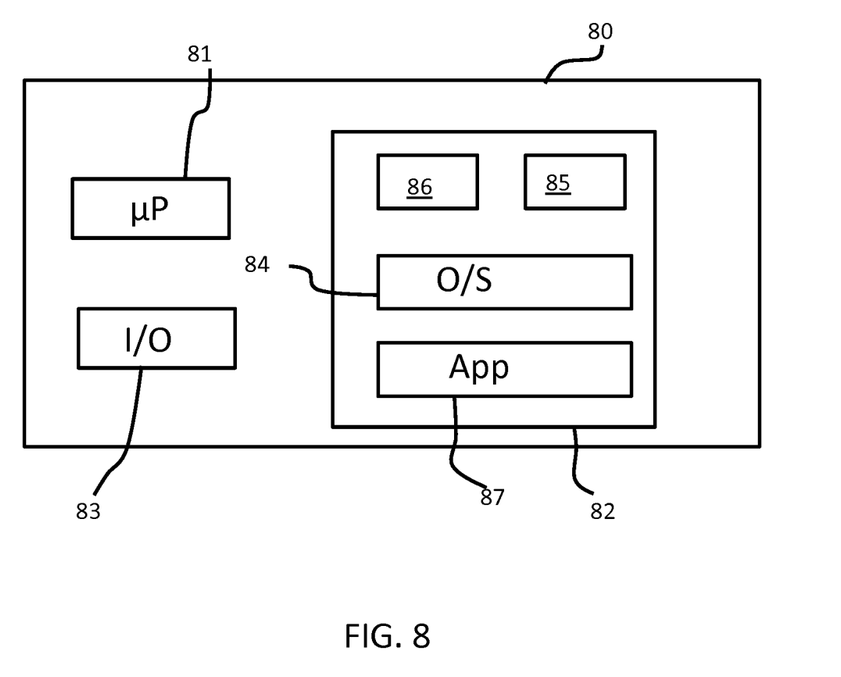
FIG. 8 shows a general computer architecture which may be used to implement the system of the invention.

The processor 6 calculates the physical activity ratio by dividing the first overall value by the second overall value. In this way, the processor 6 determines the ratio of the level of physical activity of a subject 10 during the daytime to the level of physical activity of the subject 10 during the night-time. The processor 6 outputs this data to a memory (FIG. 8).

The processor 6 may be configured to calculate the physical activity ratio on a daily basis. Alternatively, the processor 6 may be configured to calculate the physical activity ratio over a longer time period, for example on a weekly or monthly basis, according to the requirements of the user. In this way, the physical activity ratio provides an objective way to continuously monitor a subject and obtain data that can be used to assess the health status of a subject.

The processor 6 is configured to calculate a first risk score which indicates the likelihood that the subject has a severe respiratory disease. The processor calculates the first risk score by comparing the physical activity ratio to an activity ratio threshold value which represents the minimum value of the physical activity ratio associated with non-severe respiratory symptoms. The first risk score is output by the processor for review by the user. If it is determined that the physical activity ratio is lower than the activity ratio threshold, the processor 6 calculates a second risk score which indicates the severity of the symptoms, and is based on the magnitude of the physical activity ratio.

The second risk score indicates the severity of disease progression. The risk score may be stored in the memory (FIG. 8). The processor 6 is configured to determine whether the second risk score has increased and, if the second risk score has increased, the processor outputs the second risk score as an alert, to inform the user (the subject, carer or medical professional) of a change in disease progression.

The processor outputs the physical activity ratio together with the first overall value, which relates to the subject's level of daytime physical activity. By generating an indicator of daytime activity in combination with the physical activity ratio, assessment as to whether the subject has reduced exercise capacity or low motivation is facilitated.

Figure 2:
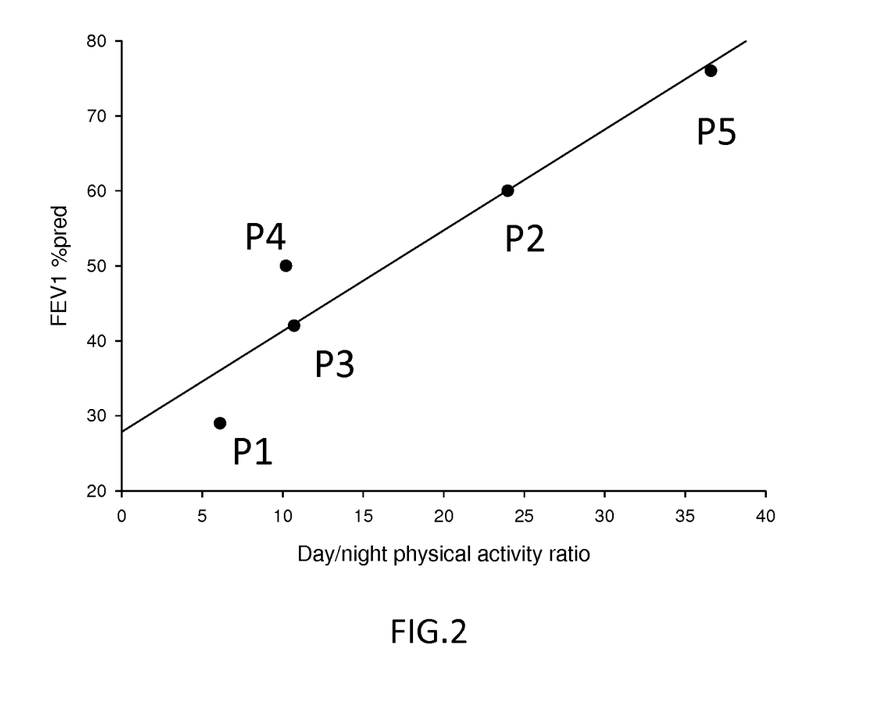
FIG. 2 illustrates the relationship between spirometry measurements (percentage of predicted forced expiratory volume in one second) and a physical activity ratio calculated according to an example.

FIG. 2 shows the relationship between the physical activity ratio, and a percent predicted value of forced expiratory volume in one second (FEV1% pred.), which is a well-known measure of respiratory disease severity. The x-axis represents the physical activity ratio and the y-axis represents the percent of predicted forced expiratory volume in one second.

The physical activity ratio data was calculated using data obtained by monitoring the physical activity of four COPD patients (P1, P2, P3, and P4) and one non-COPD patient (P5). The patients were monitored continuously during the day and night, for seven days, using a physical activity monitor. The data for FEV1% predicted was obtained by carrying out a single spirometry procedure.

FIG. 2 shows that FEV1% predicted positively correlates with the ratio of daytime physical activity to night-time physical activity (the physical activity ratio). The magnitude of the physical activity ratio is low at low values of FEV1% predicted, which corresponds to the presence of severe COPD.

To examine whether the physical activity ratio correlates with FEV1% predicted, the p-value of the data was calculated. The p-value evaluates how well the sample data supports a so-called null hypothesis; the p-value is the probability of obtaining an effect at least as extreme as the one in the sample data, assuming the truth of the null hypothesis. If the p-value is low (below 0.01), the null hypothesis is not well supported by the data.

Based on the data of FIG. 2, the p-value associated with the null hypothesis that the physical activity ratio does not correlate with FEV1% predicted is 0.0025, which indicates that the observed correlation between the physical activity ratio and FEV1% predicted is statistically significant. Thus, the physical activity ratio is an excellent parameter to support diagnosis of respiratory disease severity. Therefore, daily measures of the physical activity ratio can be used to continuously (e.g. daily, weekly or monthly) assess respiratory disease severity and progression.

Figure 3:
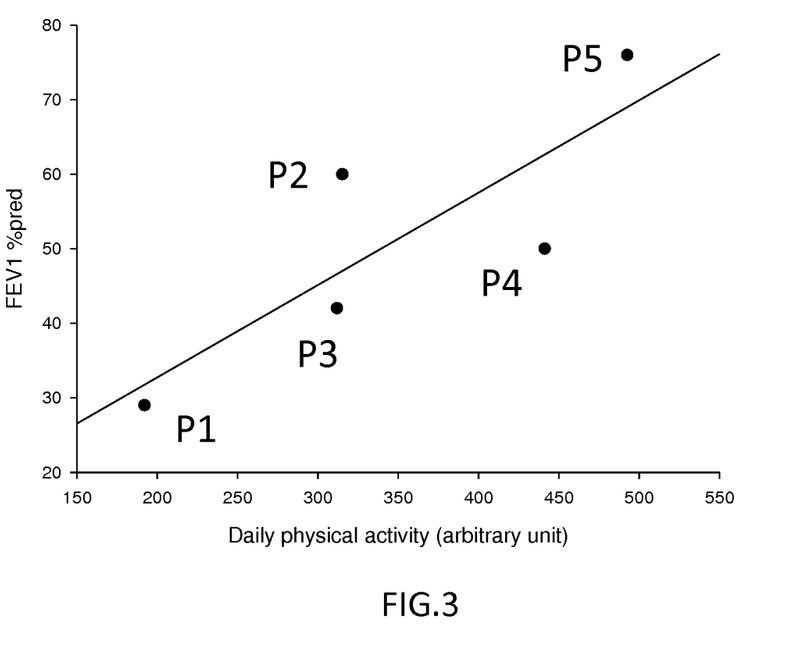
FIG. 3 illustrates the relationship between spirometry measurements (percentage of predicted forced expiratory volume in one second) and measurements of daytime activity levels.

FIG. 3 shows the relationship between daily activity (arbitrary units) and a percent predicted value of forced expiratory volume in one second (FEV1% predicted). FIG. 3 shows that higher disease severity (low FEV1% predicted) correlates with low daily physical activity. However, the correlation is not as strong as with the physical activity ratio. It can be seen that low physical activity during the day does not necessarily correspond to severe COPD. For example, patient P2 has low daily physical activity and a fairly high measurement of FEV1% predicted. According to the spirometry measurement, although the patient has low levels of daytime physical activity, this is not caused by severe COPD. Therefore, daytime physical activity alone is not a reliable indicator of disease severity or progression.

Figure 4:
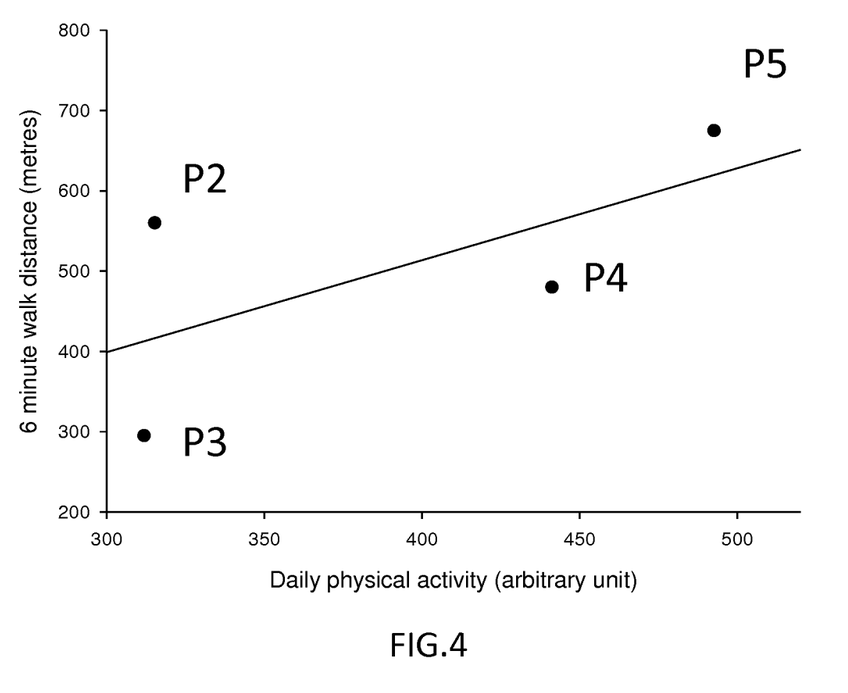
FIG. 4 illustrates the relationship between measurements of exercise capacity (as measured by the six minute walk test) and measurements of daytime activity levels.

FIG. 4 shows the relationship between daily activity (arbitrary units) and exercise capacity as measured by the six minute walk test (metres). The six minute walk distance is a well-known measure of exercise capacity, and was carried out with four subjects, having corresponding data points P2, P3, P4 and P5. FIG. 4 shows relatively weak correlation between exercise capacity and daily physical activity. This demonstrates that a patient exhibiting low physical activity during the day does not necessarily have limited capability, and therefore low activity is not an accurate indicator for exercise capacity. For example, P2 has low daytime physical activity, and a fairly high exercise capacity. Therefore, measurements of physical activity during the daytime only do not provide a reliable or accurate indicator of the impact of respiratory disease progression or severity.

Figure 5:
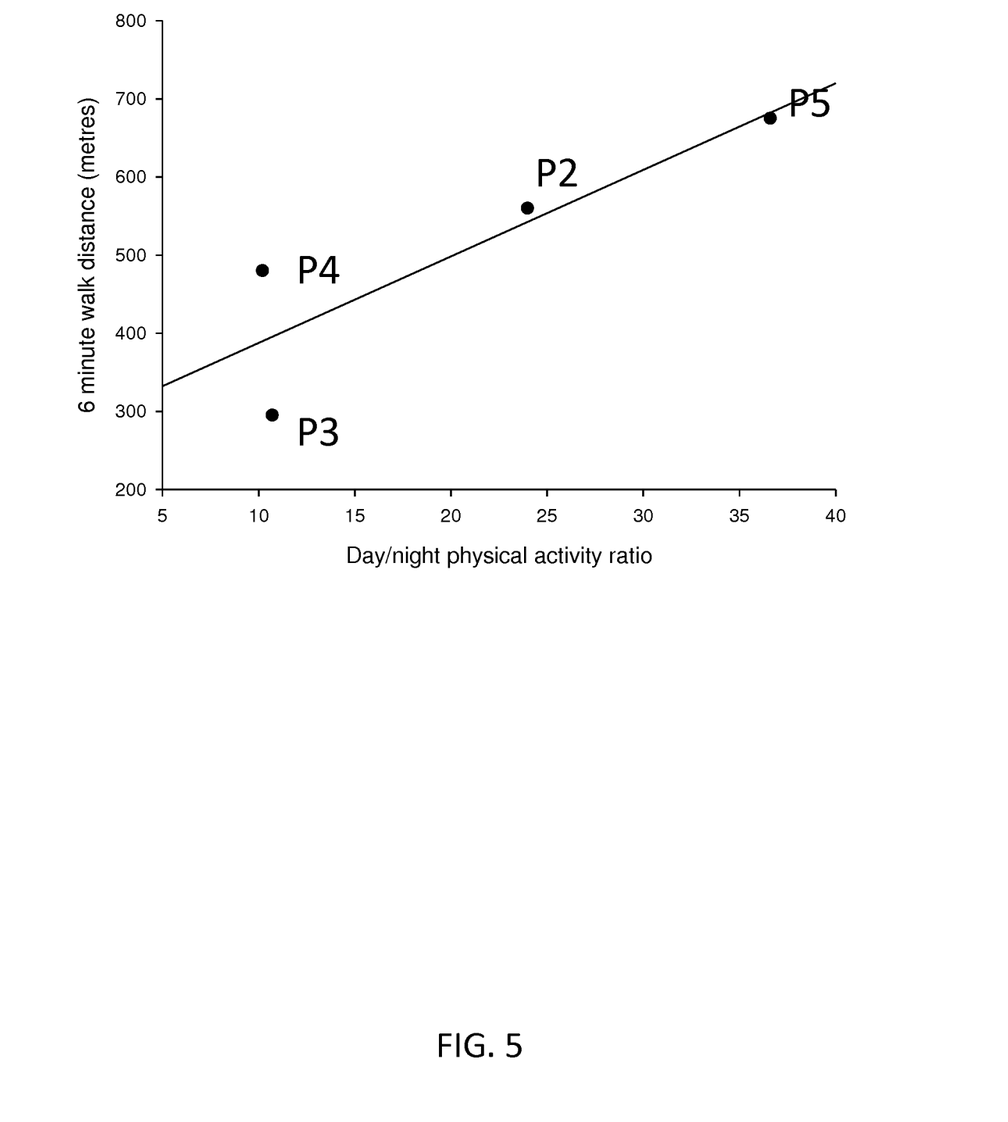
FIG. 5 illustrates the relationship between measurements of exercise capacity (as measured by the six minute walk test) and a physical activity ratio calculated according to an example.

FIG. 5 shows the relationship between the physical activity ratio and exercise capacity as measured using the 6 minute walk test (distance in metres walked in a period of 6 minutes). The outcomes of the tests are strongly correlated which indicates that the physical activity ratio provides a better indicator of exercise capacity than daily activity alone.

Therefore, as demonstrated by FIGS. 2 to 5, the physical activity ratio provides a good indicator of symptom severity and disease progression in a patient. Therefore, by continuously monitoring the physical activity of a patient, it is possible to continuously monitor the health status of a patient. This provides the additional advantage that the health status of a patient can be measured continuously. In contrast, spirometry and the six minute walk test are not appropriate for continuous assessment.

Figure 6:
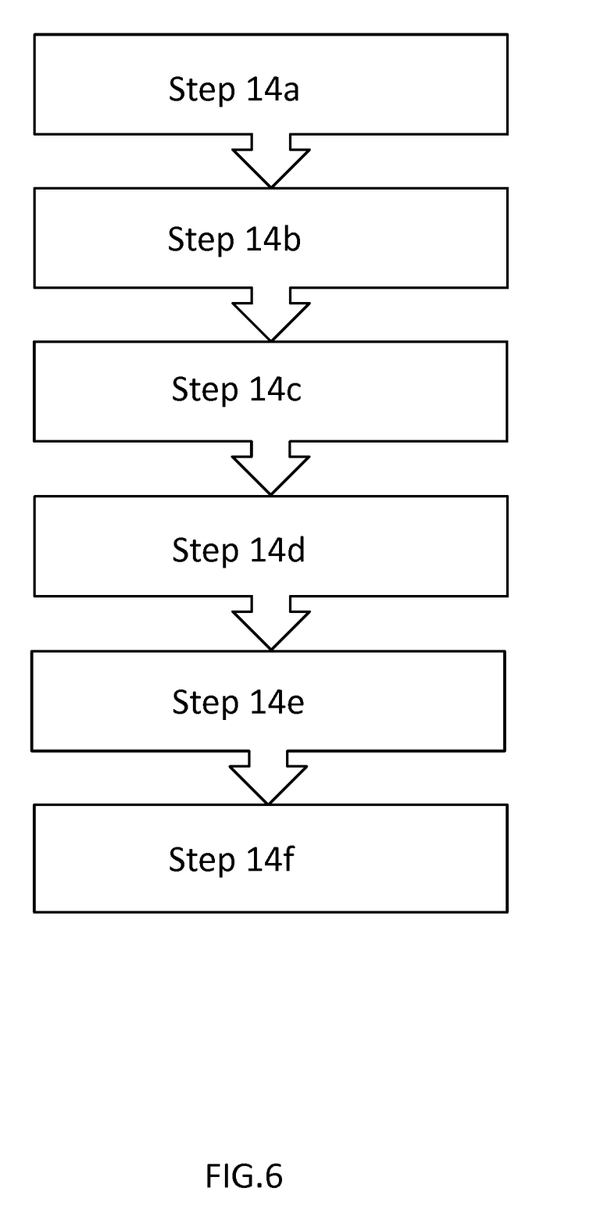
FIG. 6 illustrates the operation of a processor according to an example.

FIG. 6 illustrates the operation of the processor, according to an example. In use, the physical activity monitor obtains data relating to the physical activity levels of a subject, and transmits the physical activity data to the processor. The processor processes the data to obtain daily measures of day/night physical activity ratio together with measures of daily physical activity. This enables continuous (e.g. daily, weekly, monthly) assessment of the daily performance of physical activity as well as to detect motivational-related issues or symptom-related issues that may cause lack of physical activity. The data recorded by the physical activity monitor is loaded to a data storage device (memory) and the processor which computes the ratio between day and night physical activity as well as daily physical activity.

In an example the processor is configured to perform the procedures described above (steps 14a-14e) and is further configured to assess the overall value for daytime activity (step 14f).

In step 14a, the processor obtains a first set of physical activity data from the activity monitor. The first set of physical activity data is obtained over a first time period, which relates to daytime.

In step 14b, the processor obtains a second set of physical activity data from the activity monitor. The second set of physical activity data is obtained over a second time period, which relates to night-time.

In step 14c, the processor calculates a first overall value and a second overall value; the first overall value represents the average level of activity of the subject over the first time period and the second overall value represents the average level of activity of the subject over the second time period.

In step 14d, the processor calculates the physical activity ratio. The physical activity ratio is the ratio of the first overall value to the second overall value; therefore, it represents the ratio of average daytime activity to average night-time activity.

In step 14e, the processor compares the physical activity ratio to a threshold value. The processor creates a first risk-score for indicating the likelihood of that severe respiratory symptoms are present, or the likelihood that severe COPD symptoms are absent, based on this comparison. If the risk score corresponds to the presence of severe COPD symptoms, the processor also calculates a second risk score, based on the magnitude of the physical activity ratio.

In step 14f, the processor compares the first overall value to a daytime activity threshold value to determine whether the measurement of daily activity indicates that the subject is active or inactive.

The processor outputs at least the first risk score which indicates whether the COPD symptoms are severe and an indication of whether the first overall value indicates high or low activity (is higher or lower than the daytime activity threshold). The combination of these parameters can be used to accurately determine whether a low physical activity measurement indicates low exercise capacity as a consequence of severe COPD symptoms, or whether the low physical activity is more likely to be caused by low motivation. Therefore, by outputting information about both daytime activity and the ratio of daytime activity to night-time activity, a more complete picture of a subject's health status is provided.

Figure 7:
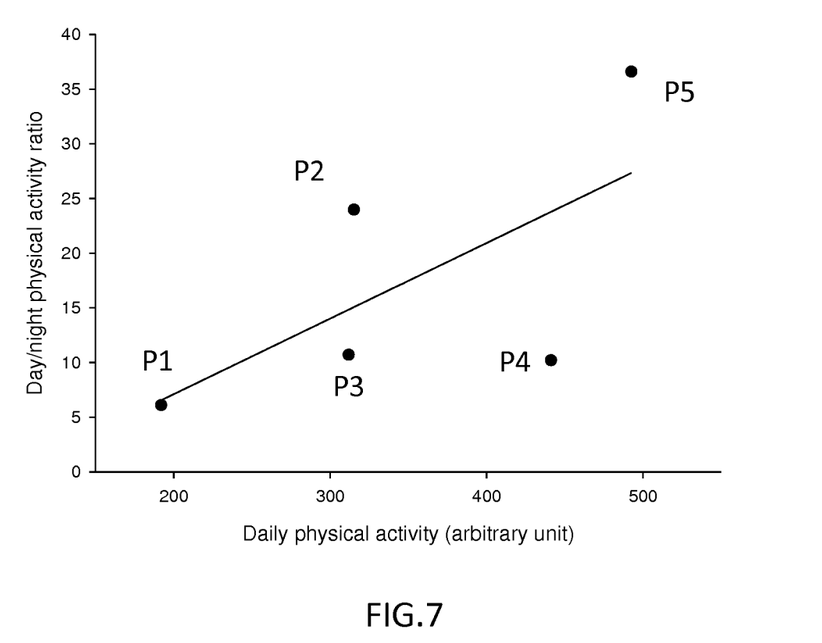
FIG. 7 illustrates the relationship between daytime activity levels and a physical activity ratio calculated according to an example.

FIG. 7 shows the relationship between the physical activity ratio and daytime activity levels (arbitrary units).

In general, a low physical activity ratio in combination with low daily physical activity (e.g. P1) indicates high disease severity, whereas a high physical activity ratio in combination with a high level of daily activity indicates low or no disease severity (e.g. P5 shows low disease severity).

If the physical activity ratio of a subject is high, but the daytime activity level is low, this may indicate that the subject's lack of activity during the daytime is due to motivation related issues rather than exercise capability. For example, the spirometry measurement indicates that P2 has low symptom severity, and the six minute walk test indicates that P2 has a high exercise capacity. By measuring the physical activity ratio and the daytime activity level, it is possible to determine this information without performing either spirometry or the six minute walk test. The physical activity ratio is fairly high, which indicates that P2 does not have severe symptoms, in line with the spirometry and six minute walk test data. Further, the combination of a low daytime activity level and a high physical activity ratio indicates that the low daytime activity level is a consequence of low subject motivation, rather than low exercise capacity. Therefore, by using both of these parameters it is possible to identify the severity of the disease, and also to flag up other issues such as low motivation.

Referring to P4, the physical activity ratio is low while daytime activity is high. The high daytime activity indicates the severity of disease symptoms is low. In this case, the physical activity ratio may be low as a consequence of sleep issues. Therefore, the combination of data concerning daytime activity levels and the physical activity ratio enables the detection of sleep related issues.

In summary, a low physical activity ratio and low daily physical activity level may indicate that the lack of physical activity is caused by the severity of COPD symptoms experienced by the subject. A high physical activity ratio and high daily physical activity indicates that the subject does not have any particular issues. Therefore, determining the physical activity ratio may be used to determine whether a subject is experiencing severe COPD symptoms. A high physical activity ratio and low daily physical activity indicates that the lack of physical activity is due to low motivation of the subject. A low physical activity ratio and a high level of daily physical activity indicates that although the respiratory related symptoms are not highly severe, the subject may be experiencing sleep disturbance issues. Therefore, by comparing the physical activity ratio and the daytime activity of a subject, it is possible to gain a more complete picture of a subject's health status, since motivational or sleep related issues may be identified. Therefore, the system can be used by a clinician to better understand whether intervention should be directed more on motivating the subject or treating the disease. Further, this information can also be used to support physical activity maintenance and coaching since it may provide increased understanding as to the exercise limitation of the subject (e.g. if physical activity is low due to exercise limitation and disease severity, pushing the subject too hard may be useless and indeed may have the effect of worsening the health status of the subject).

FIG. 8 illustrates an example of a computer 80 for implementing the apparatus described above.

The computer 80 includes, but is not limited to, PCs, workstations, laptops, PDAs, palm devices, servers, storages, and the like. Generally, in terms of hardware architecture, the computer 80 may include one or more processors 81, memory 82, and one or more I/O devices 83 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 81 is a hardware device for executing software that can be stored in the memory 82. The processor 81 can be virtually any custom made or commercially available processor, a central processing unit (CPU), a digital signal processor (DSP), or an auxiliary processor among several processors associated with the computer 80, and the processor 81 may be a semiconductor based microprocessor (in the form of a microchip) or a microprocessor.

The memory 82 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 82 may incorporate electronic, magnetic, optical, and/or other types of storage media. Note that the memory 82 can have a distributed architecture, where various components are situated remote from one another, but can be accessed by the processor 81.

The software in the memory 82 may include one or more separate programs, each of which comprises an ordered listing of executable instructions for implementing logical functions. The software in the memory 82 includes a suitable operating system (O/S) 84, compiler 85, source code 86, and one or more applications 87 in accordance with exemplary embodiments.

The application 87 comprises numerous functional components such as computational units, logic, functional units, processes, operations, virtual entities, and/or modules.

The operating system 84 controls the execution of computer programs, and provides scheduling, input-output control, file and data management, memory management, and communication control and related services.

Application 87 may be a source program, executable program (object code), script, or any other entity comprising a set of instructions to be performed. When a source program, then the program is usually translated via a compiler (such as the compiler 85), assembler, interpreter, or the like, which may or may not be included within the memory 82, so as to operate properly in connection with the operating system 84. Furthermore, the application 87 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 83 may include input devices such as, for example but not limited to, an activity monitor, a sensor etc. Furthermore, the I/O devices 87 may also include output devices, for example but not limited to a display. Finally, the I/O devices 83 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 83 also include components for communicating over various networks, such as the Internet or intranet.

When the computer 80 is in operation, the processor 81 is configured to execute software stored within the memory 82, to communicate data to and from the memory 82, and to generally control operations of the computer 80 pursuant to the software. The application 87 and the operating system 84 are read, in whole or in part, by the processor 81, perhaps buffered within the processor 81, and then executed.

When the application 87 is implemented in software it should be noted that the application 87 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

In examples, the controller is configured to obtain a first set of data and a second set of data over pre-programmed time periods. For example, the controller may control the activity monitor to obtain a first set of physical activity data between 07.00 am and 23.00 pm, and to obtain a second set of data over a second time period, for example between 23.01 pm and 06.59 am. In this way, the activity monitor obtains the first and second set of data automatically. In this case, the processor need not be configured to associate the data with specific time periods.

In examples, the processor may determine the overall activity of the subject during a time period by calculating the total energy expended by the subject over the time period.

In examples, the processor may output information indicating the health status of the patient i.e. indicating that the patient has severe symptoms impacting their level of physical activity, low motivation or sleep issues.

In examples, the processor is located remotely from the activity monitor. In other examples, the processor is integrated with the activity monitor.

In examples, the activity monitor may comprise any sensor suitable for measuring physical activity whilst the subject is awake and whilst the subject is asleep. For example, the sensor may be an accelerometer based on MEMS processes or a piezoelectric element that is sensitive to body movements of the user.

In an example, the activity monitor comprises a strap or other means for attaching the activity monitor to the user. In another example, the activity monitor is integrated into a garment to be worn by the subject.

The physical activity data may contain information about whether the data collected is night-time data or daytime data. This information may be manually input by the user, who may control the activity monitor to switch between a daytime monitoring mode and night-time monitoring mode.

The apparatus may comprise a light sensor configured to obtain a light signal which indicates the light level of the environment. The apparatus may be configured to determine whether data is collected during daytime or night-time based on information obtained by the light sensor about the light level at the time the data is collected.

Other variations to the disclosed embodiments can be understood and effected by those skilled in the art in practicing the claimed invention, from a study of the drawings, the disclosure, and the appended claims. In the claims, the word comprising does not exclude other elements or steps, and the indefinite article a or an does not exclude a plurality. The mere fact that certain measures are recited in mutually different dependent claims does not indicate that a

The invention claimed is:

1. An apparatus, comprising:
   an activity monitor for measuring the physical activity of a subject; and
   a processor for processing data obtained by the activity monitor, wherein the processor is configured to:
   calculate a first overall value based on a first set of physical activity data associated with a first time period;
   calculate a physical activity ratio based on the first set of physical activity data and a second set of physical activity data associated with a second time period;
   determine respiratory disease severity information and/or respiratory disease comorbidity information based on a combination of the physical activity ratio and the first overall value;
   output an indication of severe symptoms and reduced exercise capacity based on the determined respiratory disease severity information and/or respiratory disease comorbidity information.

2. The apparatus of claim 1, wherein the processor is configured to determine respiratory disease severity information and/or respiratory disease comorbidity information based on a comparison of the physical activity ratio and the first overall value.

3. The apparatus of claim 1, wherein the processor is configured to output respiratory disease severity information and/or respiratory disease comorbidity information including one or more of psychological issues or sleep quality issues.

4. The apparatus of claim 1, wherein the respiratory disease severity information relates to chronic obstructive pulmonary disease.

5. The apparatus of claim 1, wherein the activity monitor comprises an accelerometer.

6. The apparatus of claim 1, further comprising a controller configured to control the activity monitor to obtain a first set of data during the day and a second set of data during the night.

7. The apparatus of claim 1 wherein the processor is configured to determine, for each of the first and second sets of physical activity data, whether the data set corresponds to daytime physical activity or night-time physical activity.

8. The apparatus of claim 1 further comprising a controller configured to control the activity monitor to obtain a first set of physical activity data while the subject is awake, and to obtain a second set of physical activity data while the subject is asleep.

9. The apparatus of claim 1, wherein the processor is configured to:
   calculate a second overall value based on the second set of physical activity data; and
   calculate the physical activity ratio by dividing the first overall value by the second overall value.

10. The apparatus of claim 1 wherein the processor is configured to determine respiratory disease severity information and/or respiratory disease comorbidity information based additionally on an activity ratio threshold value.

11. The apparatus of claim 1, wherein the processor is configured to determine respiratory disease severity information and/or respiratory disease comorbidity information based additionally on a daytime activity threshold value.

12. The apparatus of claim 1, wherein the processor is configured to determine respiratory disease severity information and/or respiratory disease comorbidity information based additionally on:
    the magnitude of the physical activity ratio relative to the magnitude of an activity ratio threshold value; and
    the magnitude of the first overall value relative to the magnitude of a daytime activity threshold value.

13. A method, comprising:
    obtaining a first set of physical activity data by measuring physical activity over a first time period using an activity monitor;
    obtaining a second set of physical activity data by measuring physical activity over a second time period using the activity monitor;
    calculating, using a processor operatively coupled to the activity monitor, a first overall value based on the first set of physical activity data;
    calculating, using the processor, a physical activity ratio based on the first set of physical activity data and the second set of physical activity data;
    determining, using the processor, respiratory disease severity information and/or respiratory disease comorbidity information based on a combination of the physical activity ratio and the first overall value;
    outputting, using the processor, an indication of severe symptoms and reduced exercise capacity based on the determined respiratory disease severity information and/or respiratory disease comorbidity information.

14. The method of claim 13 further comprising calculating a second overall value based on the second set of physical activity data, wherein the physical activity ratio is a ratio of the first overall value and the second overall value.

15. A computer program product comprising a non-transitory computer-readable medium encoded with computer-executable instructions which, when executed by a processor, cause the processor to perform the method of claim 13.

* * * * *